United States Patent [19]

Kuroda et al.

[11] Patent Number: 5,298,397
[45] Date of Patent: Mar. 29, 1994

[54] METHOD OF ASSAYING D-VANILLYLMANDELIC ACID

[75] Inventors: Manami Kuroda, Choshi; Masahito Sugi, Oi, both of Japan

[73] Assignee: Yamasa Shoyu Kabushiki Kaisha, Chiba, Japan

[21] Appl. No.: 690,971
[22] PCT Filed: Oct. 10, 1990
[86] PCT No.: PCT/JP90/01344
§ 371 Date: Jun. 19, 1991
§ 102(e) Date: Jun. 19, 1991
[87] PCT Pub. No.: WO91/06005
PCT Pub. Date: May 2, 1991

[30] Foreign Application Priority Data

Oct. 19, 1989 [JP] Japan .................................. 1-272538

[51] Int. Cl.$^5$ .......................... C12Q 1/00; G01N 33/53
[52] U.S. Cl. .................................... 435/7.93; 435/7.9; 436/518; 436/536; 436/547; 436/548; 530/388.9
[58] Field of Search ............... 436/518, 536, 547, 548; 530/388.9; 435/7.9, 7.93

[56] References Cited

PUBLICATIONS

Yoshioka et al., Chem. Abst. vol. 107 (1987) p. 147,514g.

Primary Examiner—Sam Rosen
Attorney, Agent, or Firm—Wenderoth, Lind & Ponack

[57] ABSTRACT

The present invention is concerned with a method of assaying D-vanillylmandelic acid (D-VMA) contained in a specimen of a living organism through the following steps (A) to (D), and a reagent and a kit used for the assay, wherein a racemic mixture of VMA is used as the standard substance for preparing a calibration curve and a labeled anti-D-VMA antibody is used as the labeled anti-VMA antibody to specifically assay only D-VMA in the specimen:

(A) the step of conducting a competitive reaction of VMA in the specimen and VMA in solid phase against the labeled anti-VMA antibody;

(B) the step of separating the liquid phase from the solid phase;

(C) the step of determining the quantity of labeling of the labeled anti-VMA antibody combined with the solid-phase VMA and that of other substances; and (D) the step of preparing a calibration curve or obtaining an equation by using a standard substance of a known concentration, calculating the concentration of VMA corresponding to the quantity of labeling determined in the step (C) by using the calibration curve or equation thus obtained, and defining the concentration thus calculated as the concentration of VMA contained in the specimen.

4 Claims, 1 Drawing Sheet

METHOD OF ASSAYING D-VANILLYLMANDELIC ACID

TECHNICAL FIELD

This invention relates to a method of assaying D-vanillylmandelic acid contained in a specimen of a living organism and a reagent and a kit used for the assay.

BACKGROUND ART

As tumor producing acidic catecholamine metabolites, pheochromocytoma and neuroblastoma have been known. Neuroblastoma is generated primarily in infants and has been one of the assaying items of mass screening in Japan.

Presence of neuroblastoma in vivo has been determined by assaying vanillylmandelic acid (VMA) and homovanilic acid (HVA), which are acidic catecholamine metabolites, in urine.

As methods used for assaying VMA and HVA in urine, qualitative methods such as spot test and dip test and quantitative methods such as high performance liquid chromatography (HPLC) and immunoassay have hitherto been reported. The spot test and the dip test suffer from high appearance ratio of false positive, and thus they are not quite satisfactory. On the other hand, HPLC is an excellent method which is reliable with respect to precision, but a skilled specialist is required for maintenance and management of the device. Also it has a drawback in that a plurality of test samples cannot be treated at the same time.

In contrast, immunoassay has been expected to overcome the drawbacks as mentioned above [see Japanese Patent Laid-Open Publications Nos. 123765/1985 and 11165/1987; Biogenic Amines, 4, No. 3, 229–235 (1987); Infant Cancer, 24, 250–252 (1988); Revised Neuroblastoma Mass Screening, 148–152 (1989), published by Shakai Fukushi Hojin Onshi Zaidan Boshi Aiikukai; Journal of Immunological Methods, 118, 101–107 (1989)].

VMA, as shown by the following formula, has an asymmetric carbon in the molecule, and two optical isomers with different optical activities (D form and L form) exist.

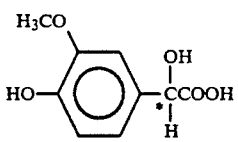

wherein * represents asymmetric carbon.

However, there is nothing in the articles hitherto published or reported in the art which teaches or suggests as to whether D-VMA can be specifically assayed by means of immunoassay.

DISCLOSURE OF THE INVENTION

We have conducted extensive research in order to develop a method of assaying D-VMA specifically and simply. As a result, we have successfully obtained an anti-D-VMA antibody and established a method of assaying specifically D-VMA contained in a specimen of a living organism according to an extremely simple method with the use of said antibody, whereby the present invention has been accomplished.

More specifically, the present invention is concerned with a method of assaying D-VMA contained in a specimen of a living organism through the following steps (A) to (D), wherein an equal amount mixture of D-VMA and L-VMA (a racemic mixture of VMA) is used as the standard substance for preparing a calibration curve, a labeled anti-D-VMA antibody is used as the labeled anti-VMA antibody, and the concentration of D-VMA contained in the specimen is calculated by using the results obtained in the step (D):

(A) the step of conducting a competitive reaction of VMA in the specimen and VMA in solid phase against the labeled anti-VMA antibody by the use of the solid-phase VMA obtained by combining VMA with a solid phase and the labeled anti-VMA antibody;

(B) the step of separating the liquid phase from the solid phase and washing the solid phase, if necessary;

(C) the step of determining the quantity of labeling of the labeled anti-VMA antibody combined with the solid-phase VMA or the quantity of labeling of other substances; and (D) the step of obtaining a curve (a calibration curve) or an equation exhibiting the relationship between the quantity of labeling and the VMA concentration by practicing the same procedure as in the above steps (A) to (C) except for using VMA of a known concentration (a standard substance) in place of the specimen, calculating the concentration of VMA corresponding to the quantity of labeling determined in the above step (C) by using the calibration curve or equation thus obtained, and defining the concentration thus calculated as the concentration of VMA contained in the specimen.

Also, the present invention relates to an anti-D-VMA antibody reagent for use in the above assay having the characteristics of (1) to (3) set forth below:

(1) Affinity: it reacts specifically with D-VMA;
(2) Cross-reactivity: the reactivity with L-VMA is 1% or lower when the reactivity with D-VMA is defined as 100%;
(3) Class: it belongs to IgG.

Further, the present invention relates to a kit for determining D-VMA in the above assay comprising reagents (1) and (2) set forth below:

(1) the above labeled anti-D-VMA antibody reagent; and
(2) a solid-phase VMA reagent.

BEST MODE FOR PRACTICING THE INVENTION

I. Assay of D-VMA

Figure 1:
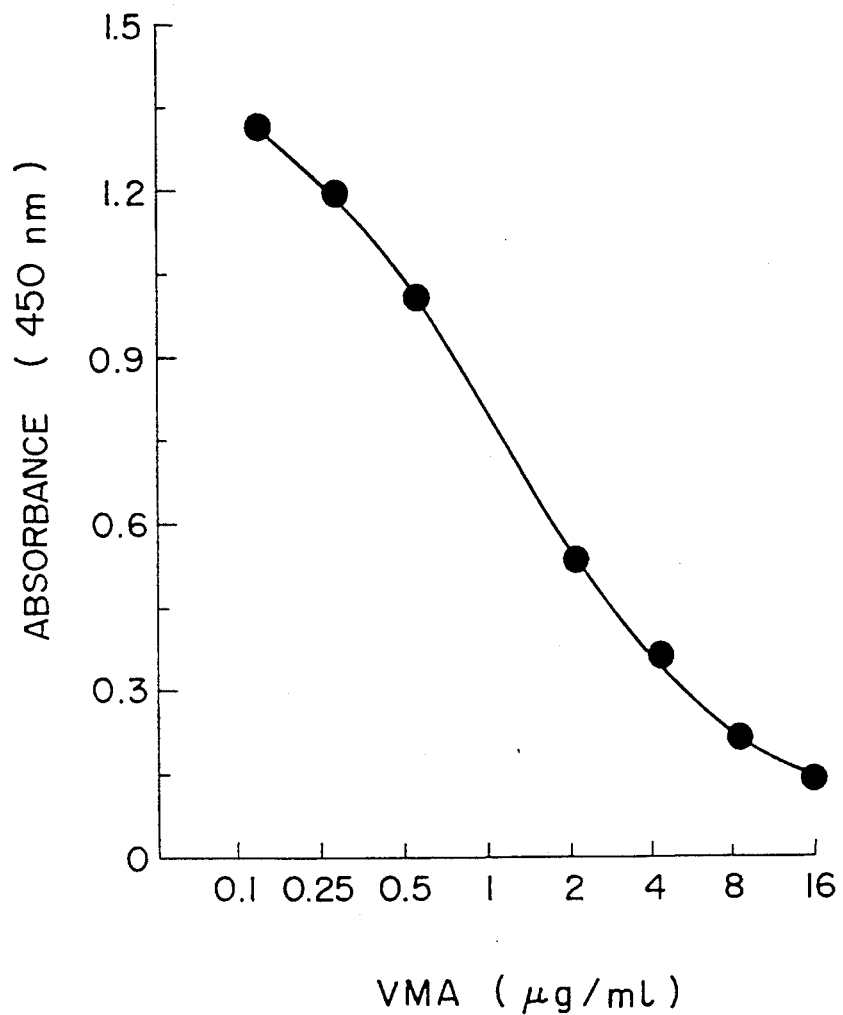
FIG. 1 is a graph showing the calibration curve prepared by the use of a racemic mixture of VMA (DL-VMA) as the standard substance.

The method of the present invention comprises the four steps (A) to (D) as mentioned above.

Step (A)

As the specimen of a living organism to be used in the step (A), those specimens that contain or may contain D-VMA, such as urine, blood, body fluid, sperm, and spinal fluid can be used.

For example, when urine is used as the specimen, the original urine diluted, if necessary, with a diluent (e.g., phosphate-buffered saline, PBS) to 2 to 20-fold is used as the specimen. Also, extracted urine from the filter paper having urine absorbed therein can be used as the specimen.

The solid-phase VMA to be used in the step (A) can be prepared according to the method conventionally used for combining hapten with a solid phase. For example, the solid-phase VMA can be obtained by combining ordinarily a VMA-high molecular carrier conjugate with a solid phase such as microplate.

As the VMA to be conjugated with the high molecular carrier, D-VMA or an equal amount mixture of D-VMA and L-VMA (a racemic mixture of VMA) can be used.

As the high molecular carrier to be used for preparation of the conjugate, natural high molecular carriers conventionally used in the preparation of antibodies to hapten antigen can be used. Examples are animal serum albumins such as bovine serum albumin, rabbit serum albumin, and human serum albumin; animal serum globulins such as bovine serum globulin, rabbit serum globulin, human serum globulin, and sheep serum globulin; animal thyroglobulins such as bovine thyroglobulin and rabbit thyroglobulin; animal hemoglobins such as bovine hemoglobin, sheep hemoglobin, and human hemoglobin; and hemocyanins such as keyhole limpet hemocyanin.

Conjugation of a high molecular carrier with VMA can be practiced by applying the Mannich reaction (see Japanese Patent Laid-Open Publication No. 11152/1986).

The solid phase to be combined with the conjugate thus obtained is not particularly limited with respect to shape, size and material. For example, those which are conventionally used as the solid phase, such as microplate, disc, tube, beads, and latex can be used.

For combining the solid phase with the above conjugate, any of the adsorption method, the covalent bonding method, the ion bonding method, the crosslinking method, and the entrapping method, can be applied. Specifically, as such a binding method the method used for preparation of immobilized enzymes can be utilized, and reference can be made to textbooks, for example, "Immobilized Enzyme" (published by Kodansha K. K.), 9-75, 1975.

The anti-D-VMA antibody to be used as the labeled anti-D-VMA antibody in the step (A) can be prepared according to the method in which, for example, the conjugate of VMA and a high molecular carrier as described above is used as the immunogen, said immunogen is administered to an animal to raise an antibody recognizing D-VMA in vivo, and the antibody thus raised is obtained.

As the animal to which the immunogen is administered, any of bovine, horse, sheep, goat, rat, mouse, guinea pig, dog, pig, rabbit, monkey, pigeon, chicken, etc. can be used, particularly, mouse, rat, guinea pig, rabbit, and goat being conveniently used.

Administration of the immunogen to such animals may be practiced in a conventional manner. For example, a suspension of an adjuvant such as complete Freund's adjuvant, incomplete Freund's adjuvant, alum adjuvant, aluminum hydroxide adjuvant, or pertussis adjuvant with the immunogen as described above is prepared and injected intravenously, intraperitoneally, subcutaneously or intradermally to the animals mentioned above.

The dose is suitably of the order of 0.01 to 10 mg/head as the amount of the conjugate when using rabbit or guinea pig as the animal, or of the order of 0.001 to 1 mg/head when using mouse or rat.

After the first administration, a similar booster as described above can be administered about once to 5 times every 1 to 4 weeks to obtain an antibody recognizing D-VMA.

The antibody thus produced can be obtained as antiserum by collecting the blood 1 to 2 weeks after the final booster and subjecting the blood to centrifugation. When purification of the antibody is required, the antibodies existing in the antiserum can be purified by fractionation for the respective classes of the antibodies according to a suitable combination of conventional methods such as the selective fractionation utilizing solubility difference (e.g., salting out and alcohol precipitation), the fractionation utilizing charge difference (e.g., ion-exchange chromatography and electrophoresis) and the fractionation utilizing molecular weight difference (e.g. ultracentrifugation method and gel filtration method). Particularly, when an immobilized antigen obtained by immobilizing the D-VMA-high molecular carrier conjugate which was used as the immunogen is used, only the antibody recognizing D-VMA can be purified by fractionation.

Next, as to the preparation of the monoclonal antibody, said monoclonal antibody can be prepared by applying suitably any of the cell fusion methods, the transformation methods with Epstein-Barr (EB) virus, etc., known in the art.

Referring to the cell fusion method suitable for bulk production of monoclonal antibodies as an example, the monoclonal antibody recognizing D-VMA can be obtained according to, for example, the procedure as described below.

a) Preparation of antibody-producing cells:

The above-mentioned immunogen is administered to an animal, preferably mouse, rat, etc. similarly as in the case of antiserum, and antibody-producing cells such as spleen cells, lymph node cells, and peripheral blood lymphocytes from the animal which has acquired immunity are obtained in a conventional manner.

b) Preparation of myeloma cells:

As myeloma cells, cell lines derived from various animals such as mouse, rat and human and generally available to those skilled in the art are employed. Preferably, the cell line to be used should have drug resistance and have the properties of being not viable in a selective medium under unfused state, but viable only under the state fused with the antibody-producing cells. Generally, 8-azaguanine resistant cell line is used, and this cell line is defective in hypoxanthine guanine phosphoribosyltransferase and cannot grow in hypoxanthine-aminopterin-thymidine (HAT) medium. Also, as a property of the cell, it is preferable that the cell line be of the so-called non-secretor type which secrets no immunoglobulin.

Specific examples of myeloma cell lines are mouse myeloma cell lines such as P3X63Ag8 (ATCC TIB-9) (Nature, 256, 495–497 (1975)), P3X63Ag8 U.1 ($P_3U_1$) (ATCC CRL-1597) (Current Topics in Microbiology and Immunology, 81, 1–7 (1978), P3X63Ag8. 653 (ATCC CRL-1580) (J. Immunology, 123, 1548–1550 (1979)), P2/NSI/1-Ag4-1 (ATCC TIB-18) (European J. Immunology, 6, 511–519 (1976)), and Sp2/O-Ag14 (ATCC CRL-1581) (Nature, 276, 269–270 (1978)); rat myeloma cell lines such as 210.RCY.Ag 1.2.3 (Y3-Ag1.2.3) (ATCC CRL-1631) (Nature, 277, 131–133 (1979)); human myeloma cell lines such as U-266-AR$_1$ (Proc. Natl. Acad. Sci. U.S.A., 77, 5429 (1980)), GM1500 (Nature, 288, 488 (1980)) and KR-4 (Proc. Natl. Acad. Sci. U.S.A., 79, 6651 (1982)).

c) Cell fusion:

For cell fusion, myeloma cells compatible with the antibody-producing cells are selected. Cell fusion can be practiced by mixing $10^7$ to $10^8$ myeloma cells/ml with antibody-producing cells at a mixing ratio of 1:4 to 10 in a medium for culturing animal cells such as Eagle's minimum essential medium (MEM), Dulbecco's modified Eagle's medium (DMEM) and RPMI 1640 medium, and contacting the cells mutually with one another at 37° C. for 1 to 10 minutes, whereby cell fusion can be effected with good efficiency. For promoting cell fusion, a fusogen such as a polyethylene glycol (PEG) having an average molecular weight of 1,000 to 6,000, a polyvinyl alcohol or Sendai virus can be used.

Also, by means of a commercially available cell fusion device utilizing electric pulses, the antibody-producing cells and the myeloma cells can be fused together.

d) Selection of hybridoma in selective medium:

As a method for selecting the desired hybridoma from the cells after cell fusion treatment, the method of utilizing selective proliferation of cells in a selective medium can be employed. For example, after diluting appropriately the cell suspension with RPMI 1640 medium containing 15% fetal calf serum (FCS), etc., the diluted suspension is seeded at about $10^5$ to $10^6$ cell/well on a microplate, and a selective medium (e.g., HAT medium) is added into each well, which step is followed by culturing with appropriate exchange of the selective medium. When 8-azaguanine resistant cell line is used as the myeloma cell and a HAT medium as the selective medium, unfused myeloma cells will die by about 10 days after cultivation. Also antibody-producing cells which are normal cells cannot grow in vitro for a long time, and therefore the cells grown on the 10th to 14th day after cultivation can be obtained as hybridomas.

e) Screening of hybridomas producing monoclonal antibody recognizing D-VMA:

Screening of the hybridomas producing the monoclonal antibody recognizing D-VMA can be practiced according to, for example, enzyme immunoassay (EIA, ELISA), or radioimmunoassay (RIA). For example, into a 96-well microplate for ELISA having the above immunogen (particularly, the conjugate of D-VMA and a high molecular carrier) or the high molecular carrier adsorbed thereon is added a culture supernatant containing the monoclonal antibody to allow the antibody to react with the immunogen or the high molecular carrier. Then the bound specific antibody is allowed to react with an enzyme-labeled antiimmunoglobulin antibody, or with a biotin-labeled antiimmunoglobulin antibody and thereafter avidin D-enzyme-labeled material, which step is followed by addition of an enzyme substrate into each well to cause color formation. By selecting a culture supernatant which causes color formation in the well having the immunogen fixed thereon but does not cause color formation in the well having the high molecular carrier fixed thereon, a hybridoma producing the antibody which reacts specifically with D-VMA can be screened.

f) Cloning:

Cloning of the hybridomas can be practiced according to, for example, the limiting dilution method, the soft agar method, the fibrin gel method and the fluorescence-activated cell sorter method.

g) Production of monoclonal antibody:

As the method for producing the monoclonal antibody from the hybridoma thus obtained, a conventional cell cultivation method or ascites formation method can be employed.

In the cell cultivation method, the hybridoma is cultured in a medium for culturing animal cells such as RPMI 1640 medium containing 10 to 15% FCS or serum-free medium, and the antibody can be obtained from the culture supernatant.

In the method of recovering the antibody from ascites, after a mineral oil such as pristane (2,6,10,14-tetramethylpentadecane) has been administered intraperitoneally into an animal the major histocompatibility of which coincides with the hybridoma, for example, in the case of mouse, the hybridoma is intraperitoneally administered in an amount of about $10^7$ cells/head. Hybridomas will form ascitic tumors within about 10 to 18 days to produce antibodies at a high concentration in serum and ascites.

When purification of the antibody is required, it can be carried out by selecting and combining suitably known methods such as the ammonium sulfate salting-out method, ion exchange chromatography utilizing anion exchanger such as DEAE cellulose, affinity chromatography using Protein A-SEPHAROSE and molecular sieve chromatography.

The antibody thus obtained is labeled and provided for the method of the present invention.

The antibody used can be the antibody itself, but in the sense of preventing nonspecific adsorption, it is preferable to use active fragments of the antibody.

The active fragment of the antibody can be any one, provided that it can maintain the characteristics of the antibody (e.g., various fragments such as $F(ab')_2$, Fab', Fab, etc.). These active fragments can be prepared by applying known methods such as the method in which the purified antibody is subjected to limited digestion by the use of a protease such as papain, pepsin, or trypsin (e.g., see "Study Methods in Immunobiochemistry (Supplemental Lectures on Biochemical Experiments 5)", edited by Biochemical Society of Japan, 89 (1986)).

As the labeling agents to be bound to the antibody, radioisotopes (e.g., $^{38}P$, $^3H$ and $^{14}C$); enzymes (e.g., β-galactosidase, peroxidase, alkaline phosphatase, glucose-6-phosphate dehydrogenase, catalase, glucose oxidase, lactate oxidase, alcohol oxidase and monoamine oxidase); coenzyme/prosthetic groups (e.g., FAD, FMN, ATP, biotin and heme); fluorescent dyes such as fluorescein derivatives (e.g., fluorescein isothiocyanate and fluorescein thioflubamyl), rhodamine derivatives (e.g., tetramethyl-rhodamine B isothiocyanate), umbelliferone and 1-anilino-8-naphthalenesulfonic acid; luminol derivatives (e.g., luminol, isoluminol and N-(6-aminohexyl)-N-ethylisoluminol) can be used.

Binding of the antibody or its active fragments with the labeling agents can be practiced according to a method suitably selected from known methods as described in textbooks [e.g., "Supplemental Lectures on Biochemical Experiments 5, Study Methods in Immunobiochemistry" published by Tokyo Kagaku Dojin K. K. in 1986, 102–112].

In the step (A), the solid-phase VMA and VMA in the specimen as described above are allowed to react competitively against the labeled anti-D-VMA antibody. The reaction can be practiced by effecting contact at 4 to 50° C., preferably 20° to 40° C., for 0.1 to 10 hours, preferably for about 0.5 to 2 hours.

Step (B)

In the step (B) of the method of the present invention, after completion of the step (A), the liquid phase is separated from the solid phase (B/F separation), and the solid phase is washed, if necessary.

The B/F separation can be carried out according to any method, if it can remove the liquid phase from the solid phase. Specifically, when a microplate, tube, etc. is used as the solid phase, the liquid phase can be physically removed by slanting, washing, reversing or rotating the solid phase. On the other hand, when a granular solid phase such as beads or latex is employed, the liquid phase can be separated from the solid phase according to such a method as filtration, centrifugation, aspiration, or washing.

After B/F separation, the solid phase can be washed by the use of a buffer such as PBS or a salt solution such as aqueous sodium hydroxide. Also, washing may be carried out simultaneously with B/F separation.

Step (C)

The step (C) of the method of the present invention is the step of determining the quantity of labeling of the labeled anti-D-VMA antibody combined with the solid-phase or that of other substances.

Determination of the quantity of labeling can be practiced by the use of a conventional method used for determining the labeling depending on the kind of the label employed.

For example, when a radioisotope is used as the label, the quantity of labeling can be determined by the use of a liquid scintillation counter, etc. On the other hand, when an oxidoreductase such as peroxidase, catalase, glucose oxidase, lactate oxidase, alcohol oxidase, or monoamine oxidase, is used as the label, by the use of hydrogen peroxide ($H_2O_2$) as the substrate and o-phenylenediamine, 2,2'-aminobis(3-ethylbenzthiazoline sulfonate)ammonium salt (ABTS), 3,3',5,5'-tetramethylbenzidine (TMBZ), etc. as the chromogenic reagent, while when $\beta$-galactosidase is used as the label, by the use of fluorescein-di-($\beta$-D-galactopyranoside) as the substrate, the absorbance or fluorescence intensity in the solution after the reaction is determined.

Step (D)

In the step (D), from the calibration curve prepared by the use of VMA racemic mixtures of known concentrations, the concentration of D-VMA corresponding to the quantity of labeling of the specimen determined in the step (C) as described above is calculated.

The calibration curve used in the present invention is prepared by the use of a racemic mixture of VMA as the standard substance. VMA is generally commercially available in the form of a racemic mixture. The racemic mixture can be optically resolved, but the operations are cumbersome, and also the resolution yield is unsatisfactory. For this reason, the method of using a racemic mixture itself as the standard substance is more convenient.

The simplest method of calculating D-VMA in the step (D) is the method in which half of the value obtained from the calibration curve prepared by the use of a racemic mixture of VMA is defined as the concentration of D-VMA. However, in the method of the present invention, the above mentioned method is not limitative. Any method which can calculate the concentration of D-VMA from the calibration curve or the equation obtained by the use of a racemic mixture of VMA as the standard substance can be employed, such as the method in which a calibration curve is prepared using the quantity of labeling determined by the use of a racemic mixture of VMA as the ordinate axis and half of the concentration of the racemic mixture of VMA as the abscissa axis, and the concentration of D-VMA in the specimen is directly determined from said calibration curve, or the method in which a equation between the quantity of labeling determined by the use of a racemic mixture of VMA and the concentration of D-VMA in the racemic mixture of VMA is obtained by a computer, and the concentration of D-VMA in the specimen is calculated from said equation.

II. Anti-D-VMA antibody reagent

As the antibody reagent for use in the above assay, one having the following characteristics as shown in the Examples described hereinafter is preferable.

(1) Affinity: it reacts specifically with D-VMA;

(2) Cross-reactivity: the reactivity with L-VMA is 1% or lower when the reactivity with D-VMA is defined as 100%;

(3) Class: it belongs to IgG.

By the use of one having such characteristics, particularly having cross-reactivity with L-VMA of 1% or less, even when a racemic mixture of VMA is employed as the standard substance, the reactivity with L-VMA in said standard substance can be almost completely disregarded. For this reason, there is brought about an effect whereby the actually existing amount of D-VMA can be calculated according to an extremely simple method as shown in the step (D) in the above assay.

The kind of the label and the labeling method which can be employed when labeling the above antibody reagent can be those as already described in the paragraph I step (A).

III. Kit for D-VMA assay

The kit used for the assay of the present invention comprises at least the following reagents as its constituents:

(1) the above anti-D-VMA antibody reagent which is labeled;

(2) a solid-phase VMA reagent.

In the above kit, by the use of the labeled antibody reagent of the present invention of (1), the reactivity with L-VMA can be disregarded, and therefore as the VMA in the solid-phase VMA reagent of (2), not only D-VMA but also a racemic mixture of VMA can be used.

Specifically, the kit comprising an enzyme-labeled antibody reagent may consist of, for example, the following reagents:

(1) a solid-phase VMA reagent (a VMA racemic mixture combined with microplate);

(2) the above anti-D-VMA antibody reagent labeled with peroxidase;

(3) a substrate solution (hydrogen peroxide + TMBZ);

(4) an enzyme reaction stopping solution (aqueous sulfuric acid solution);

(5) a standard substance of a known concentration (a racemic mixture of VMA).

The preparation methods of the above respective reagents and the details of the assay procedure of D-VMA by the use of the kit comprising these reagents are as described below in the Examples.

Referring now to the Examples, the present invention will be described in more detail.

EXAMPLE 1

(1) Preparation of labeled anti-D-VMA antibody:

A racemic mixture of VMA (hereinafter referred to as "DL-VMA") at 0.3 mM and 100 mg of human serum albumin (HSA) were dissolved in 1.0 ml of 0.3 M sodium hydrogencarbonate solution. Then 0.2 ml of 37% formalin was added, and the pH was adjusted to 6 to 7 with 3 M sodium acetate solution. The vacant space of the stoppered test tube was replaced with nitrogen gas, and the reaction was carried out under light shielding at 20±3° C. for 70 hours. After the reaction, the mixture was dialyzed several times against distilled water at 10° C. and lyophilized to obtain a DL-VMA-HSA conjugate.

The above DL-VMA-HSA was dissolved in physiological saline (1 mg/ml) and mixed with complete Freund's adjuvant at 1:1 to form an emulsion, which was administered intraperitoneally into Balb/c mouse (female, 6 weeks old) at 50 μg/100 μl to effect priming.

After priming, immunization was effected according to the same method several times every 2 weeks, and then as the final booster, 50 μg/100 μl of the above emulsion was administered to the tail vein of the mouse.

Three days after the final booster, spleen cells of the mouse were enucleated and washed with Eagle's minimum essential medium (MEM). Mouse myeloma P3X63Ag8 U.1 ($P_3U_1$) (ATCC CRL-1597) was washed with MEM. The spleen cells and $P_3U_1$ were mixed at 10:1 and the mixture was centrifuged. To the pellets obtained was gradually added 1 ml of an MEM solution containing 50% polyethylene glycol (PEG) 1000 to cause cell fusion. Further, the MEM solution was added to make up the whole amount of 10 ml, which was then centrifuged, and the pellets obtained were suspended in an RPMI 1640 medium containing 10% fetal calf serum (FCS) to $3 \times 10^4$ cells/0.1 ml as $P_3U_1$. 0.1 ml of the suspension was apportioned to each well of a 96-well microplate. One day thereafter, 0.1 ml of HAT medium was added. Then, every 3 to 4 days, a half amount of the medium was exchanged with fresh HAT medium, and 100 μl of the supernatant in the well where growth of hybridoma was recognized (1152 strains) was sampled and diluted with 200 μl of PBS. Into each well of the 96-well microplate previously coated with HSA and the 96-well microplate coated with D-VMA-HSA (10 μg/ml) was added 50 μg of the above diluted culture supernatant. According to the ELISA method by the use of avidin D-peroxidase (produced by Vector) as the avidin D-enzyme conjugate, hydrogen peroxide and 4-aminoantipyrine-phenol as the substrate and a chromogenic reagent, 25 strains (among 1152 strains) of hybridomas producing antibodies which react with D-VMA-HSA but not with HSA were selected (primary screening). Next, to a plate coated by the addition of 50 μl per well of D-VMA-HSA (0.1 μg/ml) were added 25 μl of the culture supernatant of the hybridoma selected as described above and 25 μl of each of diluted solutions of DL-VMA (160, 32, 6.4, 1.28, 0.256, 0.05, 0 (μgDL-VMA/ml)). After one hour at room temperature, by the use of the same reagent as in the case of the ELISA method as described above except for using O-phenylenediamine as the chromogenic reagent, enzyme immunoassay was practiced according to the competitive reaction method.

By examining the difference between the absorbance at 0 μg/ml of DL-VMA and the absorbance at the respective concentrations, four kinds of hybridoma strains producing monoclonal antibodies with greater difference of absorbance at low concentrations (V901, V911, V912, V914) were selected (secondary screening).

Next, according to the limiting dilution method, hybridomas were cloned. After cloning, the cells (hybridomas) were cultured to be increased in cell number, and $3 \times 10^6$ cells/mouse were administered intraperitoneally into the mice about one month after the previous intraperitoneal administration of pristane.

Two weeks later, about 20 ml of ascites per mouse were sampled.

After dilution of about 40 ml of ascites (for 2 mice) with addition of equal amount of PBS, saturated ammonium sulfate solution was added, and the fractions precipitated under 50% saturated ammonium sulfate condition were collected by centrifugation. To the precipitated fraction was added about 10 ml of a 0.1 M trishydrochloride buffer (pH 7.2) to dissolve the same, and the solution was dialyzed against the same buffer for 2 days.

Next, the antibody solution was added into a column (22 mm×65 cm) filled with DE52 (produced by Whatman), the fractions passed directly as they were collected, and then the fractions passed through as such were added to a column (22 mm×65 cm) filled with ULTROGEL AcA44 (produced by IBF) to carry out gel filtration, whereby about 600 mg of a purified antibody was obtained.

Immunological properties of the anti-D-VMA antibodies obtained by the four hybridoma strains selected by the secondary screening are shown below. Specific affinity:

Every antibody was found to react specifically with D-VMA.

Cross-reactivity:

When the reactivity with D-VMA is defined as 100%, the cross-reactivities of the antibody with other acidic catecholamine metabolites were examined to obtain the results as shown in Table 1.

TABLE 1

| Acidic Catecholamine Metabolite | Antibody Reactivity (% by weight) |
| --- | --- |
| D-VMA | 100 |
| DL-VMA | 50 |
| L-VMA | <1 |
| Homovanilic acid (HVA) | <0.01 |
| 3,4-Dihydroxymandelic acid (DOMA) | 4 |
| 3,4-Dihydroxyphenylacetic acid (DOPAC) | <0.01 |
| Metanepherine | <0.01 |
| Vanillylpyruvic acid | 4 |

The cross-reactivity was determined by drawing standard curves for the respective acidic catecholamine metabolites, respectively, and comparing the concentration ratios of the respective acidic catecholamine metabolites at 50% inhibition (point). Subclass type:

The subclasses of the antibodies obtained were IgG-$2_a$/κ(one strain) and IgG$_1$/κ(three strains).

5 ml of the monoclonal antibody solution thus obtained (concentration: 10 mg/ml) was dialyzed against a 0.1 M acetate buffer (pH 3.9). To the monoclonal antibody solution obtained by dialysis was added 5 ml of an enzyme solution [a solution of 2 mg pepsin and 8.7 mg sodium chloride dissolved in a 0.1 M acetate buffer (pH 3.9)], and the reaction was carried out at 37° C. overnight. The reaction mixture was dialyzed against a 0.1 M borate buffer (pH 8.0), then subjected to gel filtration by the use of ULTROGEL AcA44, and the F(ab')$_2$ fractions were collected. After the F(ab')₂ fraction solution was concentrated to 4 mg/ml by the use of CENTRY FLOW (Amicon), the concentrate was dialyzed against a 0.1 M phosphate buffer (pH 6.0). Next, 11 mg of 2-mercaptoethylamine was dissolved in a 0.1 M phosphate buffer (pH 6.0) containing 5 mM EDTA, and 100 $\mu$l of the solution obtained was added to 1 ml of the F(ab')₂ solution to carry out the reaction at 37° C. for 90 minutes. After the reaction, the reaction mixture was subjected to gel filtration with SEPHADEX G25, and the protein fractions passed directly were collected and concentrated to 1 ml by the use of CENTRY FLOW to obtain a Fab' solution of anti-D-VMA monoclonal antibody.

Next, 4 mg of horseradish peroxidase (HRPO: produced by Toyo Boseki K. K.) was dissolved in 0.6 ml of a 0.1 M phosphate buffer (pH 7.0). To 1.5 mg of N-succinimidyl-4-(N-maleimidomethyl)cyclohexane-1-carboxylate (EMCS) was added N,N-dimethylformamide (DMF) to dissolve the same to 15.4 mg/ml. With 60 $\mu$l of this solution was mixed the HRPO solution previously prepared, and the reaction was carried out at room temperature for 2 hours. Next, the reaction mixture was passed through SEPHADEX G25 column (1×45 cm) for gel filtration. The absorbance at 403 nm of the eluate was measured, and the fractions passed directly as they were corresponding to HRPO were collected and concentrated to 1 ml by the use of CENTRY FLOW to obtain an HRPO solution wherein the HRPO has a maleimide moiety introduced.

One ml of the above Fab' solution and 1 ml of the HRPO solution obtained above were mixed, and the reaction was carried out at 4° C. overnight. Next, the total amount of the reaction mixture was subjected to gel filtration by the use of ULTROGEL AcA44 column (1.5×45 cm), and absorbances of the eluate at 280 nm and 403 nm were measured. The fractions in which HRPO and Fab' were estimated to be bound approximately at 1:1 were collected. After dialyzing the fractions obtained against PBS, the dialyzate was concentrated by the use of CENTRY FLOW to provide a peroxidase-labeled anti-D-VMA antibody solution.

(2) Preparation of solid-phase antigen plate: in (1) was dissolved in 5 ml of PBS to prepare an antigen solution, which was added into a 96-well microplate in an amount of 50 $\mu$l per well and left standing at room temperature for one hour to be adsorbed thereon. After the residual antigen solution was removed, each well was washed three times with PBS. Next, for blocking the antigen-unadsorbed portion of the well, PBS containing 3% gelatin was added into each well in an amount of 300 $\mu$l per well and left standing at room temperature for one hour. After removal of the residual gelatin-containing PBS, drying was performed under reduced pressure to prepare a solid-phase antigen plate.

(3) Preparation of D-VMA and L-VMA:

A DL-VMA solution dissolved in the moving phase shown below (0.2 to 2 mg/ml: produced by Sigma) was separated into D-VMA and L-VMA using the high performance liquid chromatography (HPLC) by the use of a column for optical resolution chromatography. The separation conditions of HPLC were as shown below.

Separation conditions for D-VMA and L-VMA: Column:
   TSK gel ENANTIO L1 (4.6 mm×25 cm: produced by Toso K. K.)
Moving phase:
   0.5 mM aqueous cupric sulfate solution Flow rate:
   0.5 to 1 ml/min.
Detection:
   254 nm For the D-VMA fraction and the L-VMA fraction obtained, it was confirmed by the same HPLC method as described above that a single absorption peak was obtained for each. Since VMA's in the D-VMA fraction and the L-VMA fraction thus obtained had formed a complex with copper ion therein, the complex was decomposed by adding 0.5 ml of a 2.6% hydrochloric acid solution with respect to 0.7 ml each of the fractions. Next, 3 ml ethyl acetate was added, and sodium chloride was further added for saturation. After shaking for 10 minutes, the ethyl acetate layers containing the respective VMA's were separated. The solvent was evaporated by the use of nitrogen gas, and the residue obtained was dissolved in 300 $\mu$l of PBS to prepare a D-VMA solution or L-VMA solution.

D-VMA was identified by subjecting the D-VMA solution obtained from DL-VMA according to the method of Armstrong et al (Biochem., Biophys., Acta., 25, 442 (1957)) to the HPLC method as described above, and comparing the retention time observed.

(4) Assay of Specimen:

A volume of 50 $\mu$l of the D-VMA solution or L-VMA solution as described above and 50 $\mu$l of the peroxidase-labeled anti-D-VMA antibody solution were added into each well, and reaction was carried out stationarily at room temperature for one hour.

After reaction, the solution in each well was discarded and each well was washed with a 0.9% aqueous sodium chloride solution.

After washing, 100 $\mu$l of a substrate solution (containing 1 mM H₂O₂ and 0.25 M TMBZ) was added and left standing for 25 minutes. A volume of 100 $\mu$l of a reaction stopping solution (a 2N sulfuric acid solution) was added, and absorbance at 450 nm was measured by the use of a 96-well microplate reader MPR-A4 (produced by Toso K. K.).

After measurement, from the calibration curve prepared by the use of DL-VMA of a known concentration as a standard substance (FIG. 1), the VMA concentration corresponding to the above absorbance was determined.

Also, similar specimens were measured by the HPLC method.

The measurement conditions of the HPLC method were as shown below. Measurement conditions:
Column:
   RP-18T (4×250 mm: produced by IRICA)
Moving phase:
   phosphate buffer (pH 3.0, containing 1.36 M acetone and 0.013 mM EDTA)
Detection:
   Electrochemical detector Σ-875 (voltage 850 mV: produced by IRICA)
Flow rate:
   0.8 ml/min.

The measurement results are as shown in Table 2.

TABLE 2

| Specimen | Specimen No. | HPLC Method [1] | Method of the Present Invention [1] |
|---|---|---|---|
| D-VMA | 1 | 29.082 | *1 |
|  | 2 | 2.908 | 5.402 |
|  | 3 | 0.286 | 0.551 |
| L-VMA | 1 | 34.806 | 0.310 |
|  | 2 | 3.481 | *2 |

TABLE 2-continued

| Specimen | Specimen No. | HPLC Method [1] | Method of the Present Invention [1] |
|---|---|---|---|
| | 3 | 0.369 | *2 |

[1]: Concentration unit is μg/ml.
*1: detection limit or higher, measurement impossible
*2: detection limit or lower, measurement impossible As is apparent from Table 2, it has been clarified that the method of the present invention can assay specifically D-VMA without detecting L-VMA since the labeled antibody used has substantially no reactivity with L-VMA.

EXAMPLE 2

(1) Preparation of calibration curve by the use of D-VMA solutions:

By the use of D-VMA solutions of known concentrations as standard substances, the reaction was carried out in the same manner as in Example 1 to prepare a calibration curve.

(2) Assay of urine:

By the use of urine test samples diluted 10-fold with PBS (A, B, C) as specimens, D-VMA in urine test sample was assayed according to the method as described in Example 1. From the two calibration curves of the calibration curve in Example 1 prepared by the use of DL-VMA based on the absorbance at 450 nm (FIG. 1) and the above calibration curve prepared by the use of D-VMA based on the absorbance at 450 nm, the respective concentrations of VMA were determined.

Also, VMA concentrations of the above urine test samples were determined according to the HPLC method as described in Example 1. In the case of the HPLC method, the VMA concentrations in the test samples were calculated by the use of the two standard substances of DL-VMA and D-VMA.

The assay results of the test samples are shown in Table 3.

TABLE 3

| Assay Test Sample | HPLC Method [1] | | Method of the Present Invention [1] | |
|---|---|---|---|---|
| | Standard Substance | | | |
| | D-VMA | DL-VMA | D-VMA | DL-VMA |
| A | 2.15 | 2.00 | 1.88 | 3.16 |
| B | 1.15 | 1.04 | 0.83 | 1.95 |
| C | 0.58 | 0.52 | 0.51 | 1.04 |

[1]: Concentration unit is μg/ml.

Since D form and L form cannot be determined independently by the HPLC method, substantially equal values are obtained even by the use of D-VMA and DL-VMA as the standard substances. In contrast, since the method of the present invention uses an antibody specific for D-VMA, when DL-VMA is used as the standard substance, the antibody reacts with a half amount of the total VMA in the standard substance (content of D-VMA). Therefore, when the concentration of VMA in the urine test sample is determined by the use of the calibration curve prepared with DL-VMA as the standard substance, a value two-fold that of D-VMA actually existing in urine is obtained. For this reason, in the present invention wherein a labeled anti-D-VMA antibody is used as the labeled antibody and DL-VMA is used as the standard substance, the true value of D-VMA in the specimen can be determined by dividing the value obtained by the assay into halves.

Next, by performing analysis of the calibration curve prepared by the use of DL-VMA (FIG. 1) by means of a computer, it has been found that the following equation is valid between the absorbance (y) of the specimen obtained according to the method of the present invention and the concentration (x) of D-VMA in the specimen. Accordingly, the concentration of D-VMA can be determined directly from the following equation without preparing calibration curves. In the following equation, the coefficients (a to d) are coefficients only in the assay system employed in the present example, and thus it should be understood that they are not always constant.

$$y = \frac{a - d}{1 + (c/x)^b} + d$$

$a = 1.478$
$b = 0.9144$
$c = 0.3631$
$d = 0.02398$

UTILIZABILITY IN INDUSTRY

The method of the present invention can assay specifically D-VMA and therefore can be applied to mass screening of neuroblastoma. Also, the antibody reagent of the present invention has cross-reactivity with L-VMA of 1% or less, and therefore a racemic mixture of VMA can be used as the standard substance and as the VMA for preparing a solid-phase VMA reagent.

Further, the assay kit of the present invention including the above antibody reagent is a kit most suitable for practicing the method of the present invention.

What is claimed is:

1. A method of assaying the amount of D-vanillylmandelic acid (D-VMA) in a liquid specimen, comprising the steps of:
   (a) conducting a competitive reaction of D-VMA in the liquid specimen and D-VMA in a solid phase against a solution containing an anti-D-VMA antibody,
   (b) separating the liquid phase from the solid phase,
   (c) measuring the quantity of anti-D-VMA antibody bound to the solid phase, and
   (d) determining the quantity of D-VMA in the liquid specimen based upon the amount of anti-D-VMA antibody bound to the solid phase utilizing a standard curve prepared by conducting steps (a)–(c) using a standard sample containing a known amount of D-VMA in place of the specimen,
   wherein the anti-D-VMA antibody is capable of specifically binding to D-VMA and has a cross reactivity with L-VMA of 1% or lower based upon a reactivity with D-VMA of 100%.

2. The method according to claim 1, wherein the solid phase contains a racemic mixture of both D-VMA and L-VMA.

3. The method according to claim 1, wherein the standard sample contains a racemic mixture of both D-VMA and L-VMA.

4. The method according to claim 1, wherein after the liquid phase is separated from the solid phase in step (b), the solid phase is washed prior to measuring the quantity of anti-D-VMA antibody bound to the solid phase according to step (c).

* * * * *